United States Patent [19]

Gomez et al.

[11] 4,162,289

[45] Jul. 24, 1979

[54] FILTER UNIT FOR AVOIDING ENVIRONMENTAL POLLUTION IN CEMETERIES

[75] Inventors: Carlos R. Gomez; Horst Eller, both of Mexico City, Mexico

[73] Assignee: Internacional de Ciencia y Tecnologia, S.A., Mexico City, Mexico

[21] Appl. No.: 772,046

[22] Filed: Feb. 25, 1977

[51] Int. Cl.$^2$ .................. B01J 8/04; E04H 13/00; B01D 53/04

[52] U.S. Cl. ......................... 422/170; 422/5; 422/900; 422/4; 55/316; 55/387; 52/130

[58] Field of Search .................. 52/128–132; 423/245, 230, 228; 21/74, 75, 53 R, 54 R; 210/501; 424/145, 148, 125; 55/316, 387, 318; 422/5, 30, 170; 23/284, 288 F, 288 FA, 288 FB

[56] References Cited

U.S. PATENT DOCUMENTS

| | | | |
|---|---|---|---|
| 949,032 | 2/1910 | Ernsberger | 21/75 |
| 1,029,203 | 6/1912 | Loewenthal | 424/148 |
| 1,087,448 | 2/1914 | Holway | 52/131 |
| 1,156,039 | 10/1915 | Rothenberger | 52/130 |
| 1,189,203 | 6/1916 | Kern et al. | 21/75 |
| 1,716,479 | 6/1929 | Bilsky | 23/288 FB |
| 1,931,989 | 10/1933 | Jenness | 23/288 FB |
| 1,964,808 | 7/1934 | Bottoms | 423/228 |
| 2,040,806 | 5/1936 | Feigl | 210/501 |
| 2,172,314 | 9/1939 | Adams et al. | 424/145 |
| 2,325,657 | 8/1943 | Burkness | 55/316 |
| 2,517,209 | 8/1950 | Jackson et al. | 23/288 FB |
| 2,701,781 | 2/1955 | Guevara et al. | 424/148 |
| 2,777,759 | 1/1957 | Sokolik | 23/288 FB |
| 2,785,962 | 3/1957 | Ruth | 23/288 FB |
| 2,998,308 | 8/1961 | Ruth | 23/288 F |
| 3,130,520 | 4/1964 | Newman | 52/135 |

FOREIGN PATENT DOCUMENTS 19262 of 1912 United Kingdom ............... 21/75

OTHER PUBLICATIONS

Merck Index, 9th Edition, Mercuric Chloride & Copper Sulfate.

Primary Examiner—Michael S. Marcus
Attorney, Agent, or Firm—Ladas, Parry, Von Gehr, Goldsmith & Deschamps

[57] ABSTRACT

The present invention relates to filtering units or cartridges useful for avoiding environmental pollution resulting from the decomposition of corpses in cemeteries. The units or cartridges comprise a non-porous container with an inlet for gases at one end and an outlet duct having its entrance within and proximate the opposite end. Gases entering said container through the inlet pass through at least the greater part of said container before reaching the outlet. A plurality of selective filtering zones lie within said container selectively to operate on gases passing through the filter from the inlet to the outlet. These zones, which may be separated by separators, including an inert and porous material to act both as a filter for bacteria and as a layer to retain the remaining filtering material in position, a layer of acidic material to eliminate amines, a layer of a metallic sulphate to remove compounds containing sulphur and a final layer of activated charcoal located proximate the outlet.

4 Claims, 1 Drawing Figure

U.S. Patent  Jul. 24, 1979  4,162,289
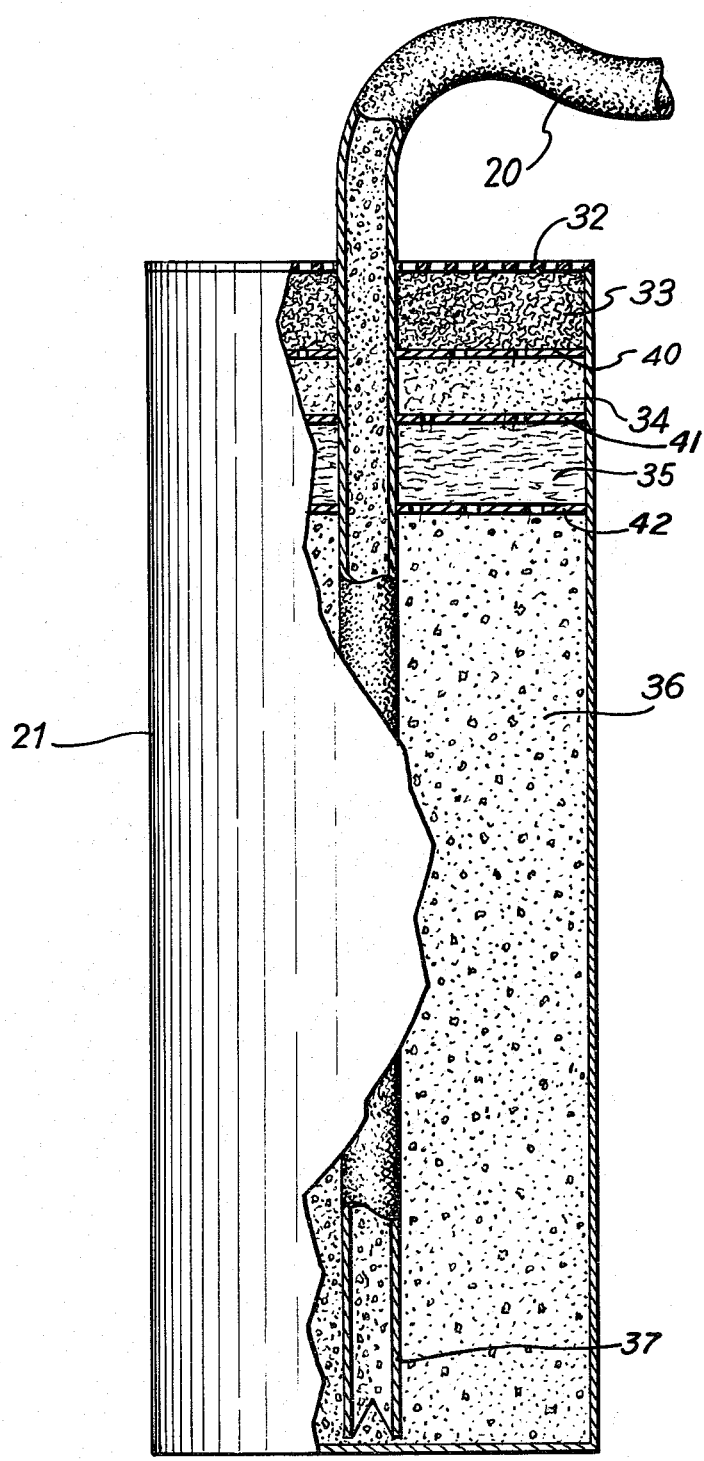

FILTER UNIT FOR AVOIDING ENVIRONMENTAL POLLUTION IN CEMETERIES

BRIEF SUMMARY OF THE INVENTION

In view of the decomposition of the corpses and in order to avoid build up of pressure of gases formed upon such decomposition, the invention provides improved filtering apparatus.

Thus, a further object of the present invention is to provide a purifying filter for the gases resulting from the decomposition or putrefaction of bodies. With the filtration inherent in the passage of said gases through several purifying layers, only innocuous gases pass to the outside atmosphere, such as carbonic acid, nitrogen, oxygen, water vapor and others that constitute the normal components of the atmosphere.

Another object of the invention is to provide a filter to purify gases as mentioned in the preceding paragraph, composed of a container having several layers through which the gases resulting from the decomposition or putrefaction must pass, so that at the end only the innocuous gases and vapors reach the outside.

Still another object of the invention is to provide a filter to purify malignant gases resulting from the decomposition or putrefaction of bodies, based on several chemical agents to eliminate successively, as the gases pass through these agents, the components that contaminate the atmosphere and produce disagreeable odors.

An additional object of the invention is to eliminate the possibility that in the discharge of dangerous gases there may also be a discharge of micro-organisms to the atmosphere. These micro-organisms are retained by some materials which are also contained in the filter provided, and which act as bacteriological filters.

The floor of each funeral vault may be sloped to capture on the floor of the crypt the liquids that are produced from the decomposition of the bodies, and a canister or adsorbent cartridge containing odor neutralizers, including bactericides and fungicides, along with solids having high power of adsorption and retention of liquids, is placed on said floor to avoid the need for drainage or septic tanks.

The funeral vaults provide for escape of the gases to a ventilation line for discharge to the atmosphere, after first being filtered through a cartridge filter than can be installed in the interior of the mortuary vault, preventing the escape of any kind of microbes and the accumulation within the crypt or vault of pressures that could be dangerous. A mechanical alarm system or an electric or electronic system can be included in each mortuary vault to permit detection of any movement of a person who might have been buried alive. There can also be included in the interior of the vault a volatile disinfectant as an additional precaution to disinfect the inside air, with the object of facilitating the evacuation of the gases produced within the vault.

The filter unit finds particular application in the vault since, as has long been known, the process of decomposition and putrefaction of bodies produces a series of substances of disagreeable odor which because of their characteristic properties are also destructive and produce inevitably a certain degree of pollution. This contamination consists of the discharge of disagreeable gases with a strong smell and also of pathogenic micro-organisms that at a given time can produce serious illnesses if they contact a living creature.

This is the reason why burial of the mortal remains of a person or animal is done in such a way as to prevent the gases and micro-organisms that come from the decomposition of such mortal remains from contaminating the atmosphere. Such decomposition normally takes place in the absence of air, that is, in an anaerobic manner. In the purifying filter of the invention such gases are retained in a special cartridge either by adsorption or by chemical reactions. Adsorption involves the physical retention of gases or parts that "adhere" to the surface of the adsorbent agent as a consequence of the electrostatic effects of Van der Waals forces. Retention by chemical reaction involves the interaction of two different substances to produce one or more different substances.

Each case of putrefaction is different from others. This is because putrefaction is controlled by different factors, such as: the prevailing temperature and humidity of the atmosphere, the chemical composition and the proportions of various substances in each body, the types of bacteria or fungus that are found in them, the causes of death, the amount of oxygen present, etc. It is however, unquestionable, and this has been proved experimentally that the principal odor agents are included in three basis groups:

(a) the amines (primary, secondary, tertiary amines, amino-acids, monoamines, diamines, etc).

(b) the sulphur compounds (mercaptans, hydrogen sulfide, cyclical compounds, etc.)

(c) the carboxylic acids (of linear or ramified chains, with several functional groups, etc.)

The amines and ammonia ($NH_3$) react rapidly with mineral acids or organic acids with a constant of dissociation, such as oxalic acid, forming the respective salts, which are generally odorless and solid.

The mercaptans and hydrogen sulfide react easily with copper sulphate, producing copper sulphide or organometallic compounds, and producing in the first case sulphuric acid ($H_2SO_4$) as a by-product, which is also capable of contributing to the fixing of amines.

The carboxylic volatile acids and other gases produced are retained by activated charcoal, by means of the adsorption phenomenon previously described.

On account of the phenomenon described and also the fact that in most cities in which there are generally great concentrations of people cemeteries often are located in areas within the metropolis or in the nearby circumferential areas, it has become necessary to find a way to avoid disagreeable odors generally produced in the cemeteries and surrounding areas. The main objectives are to prevent contamination of the environment, to avoid affecting people in the proximity of cemeteries and to give the public the confidence that adults and their children can visit the cemeteries and stay for a long time in them or in nearby areas without danger and without the inconveniences that generally occur nowadays in cemeteries.

The invention will be better understood and appreciated from reading the following description in conjunction with the drawing of the preferred embodiments of the invention.

BRIEF DESCRIPTION OF THE DRAWING

The single FIGURE is an enlarged sectional view of a filter of the invention.

DETAILED DESCRIPTION OF THE INVENTION

The drawing shows an enlarged and detailed section of the purifying filter 21, a cylindrical or other conveniently shaped container is composed of a resistant material such as plastic, metal, or any other material that is non-porous, waterproof and resistant to corrosion. The cylindrical body contains in its interior various layers of materials contained by separators 40, 41, 42, and a perforated lid 32 permits flow of gases from outside the filter to its interior. These gases pass first through a layer 33 of fiberglass which is supported by separator 40. Immediately after the layer of fiberglass, a layer 34 of oxalic acid is presented to remove the amines from the passing gases. Immediately after the oxalic acid there is a layer 35 composed of copper sulphate, which is preferable the pentahydrate so that it is not hygroscopic, which traps the aforementioned sulphur components. Thereafter a layer 36 which is substantially larger than the preceding layers and which consists of activated charcoal, is located to capture the gases such as vapors or caboxylic acids and some gases of strong odor, that pass through the preceding layers. The carbon dioxide is not retained by the activated charcoal but passes to the atmosphere without causing any problems due to the fact that it is innocuous and that it diffuses into the atmosphere.

Once the gases have circulated through the activated charcoal, they enter a duct 37, through which the filtered gases pass, now purified and innocuous, and are discharged from the coffin or crypt into the atmosphere through the ventilation line 20.

The dimensions of the filter should be such that an efficient time of contact is provided between the gases and the substances that purify them. The dimensions of the filter may vary, and it is obvious that for one crypt a filter of a given size can be used, while for a series of crypts or for a place for several bodies or where there are different possibilities of decomposition, with proportionate emission of contaminating gases, a much larger filter or a series of filters can be used.

Decomposition of a body in aerobic conditions produces disagreeable gases but these gases dilute in the atmosphere. For that reason it has been thought that aerobic putrefaction is less harmful or that it produces less disagreeable gases. It has been found, however, that aerobic decomposition, as well as anaerobic, produces contaminating gases that sicken the atmosphere and hence are uncomfortable and in certain circumstances dangerous to the human beings who live in the zones in which the decomposition takes place. Also, the bacterial contamination presents a danger, which however can be totally eliminated by the filter provided by the present invention.

The several layers of constituents inside the filter can be varied. For example, instead of a compact layer of fiberglass, cotton or other similar material can be utilized to hold in position the various layers which also act as bacteriological filters to prevent the micro-organisms from escaping to the atmosphere.

It is calculated that the successive layers of oxalic acid, copper sulphate and activated charcoal in combination neutralize all the discharges of gases that generally are produced by the decomposition of inanimate bodies of human beings or animals. For this reason, the filter has demonstrated that it works very efficiently and satisfactorily serves it function. Where the filter is used properly, there need no longer be the concern, as there has been heretofore, that in an urban or semi-urban zone or in zones near any high concentration of people, there may be a danger of air pollution or of spreading of possible illnesses among the people due to the acids and the bacteria resulting from the decomposition of bodies.

Care must be taken that the container and the connections that are made are hermetic so that the gases always pass through the filter. The gases always generate some pressure and even when this pressure is low they will pass through the filter components within the container.

The amounts of the substances that are used and that are contained in the purifying filter provided will vary, of course, according to the particular necessities of each case. Considering that a standard human body of an adult weighs 70 kilos and loses approximately 2.1 kilograms of nitrogen and 0.2 kilograms of sulphur, the following quantities of components can be used:

| Copper sulphate | from 1.0 to 10 kilograms (for multiple systems) |
|---|---|
| oxalic acid | from 0.2 to 5 Kgs |
| activated charcoal | from 1.0 to 20 Kgs |

Of course the aforementioned quantities can be varied as desired, but it has been proved experimentally that a variation of the components within the scale of amounts shown above functions satisfactorily and makes the filter work efficiently, so that the best results are always obtained.

As an alternative embodiment, the copper sulphate, which is used to retain the sulphurated gases such as the mercaptans, hydrogen sulfide, cyclical components and others, can be substituted by some salts of heavy metals, such as for example mercuric chloride or lead acetate. The objective should always be to retain such sulphurated compounds, which produce a major part of the disagreeable gases from putrefying bodies.

This invention has been described thus far according to the preferred embodiments, but it is evident that any variation made in the invention as described and claimed is within the scope and range of this invention.

We claim:

1. A filter for removing harmful gases and unpleasant odors from decomposing corpses, said filter comprising an elongated container hermetically sealed at one end and having a perforated inlet extending substantially across the opposite end, an exit duct projecting through said perforated inlet and extending through substantially the entire length of said container to terminate just short of said hermetically sealed end whereby gases entering the container through said perforated inlet end pass through substantially the entire container length before entering the exit duct for passage in the reverse direction for venting to atmosphere, first separator means located within said container and extending around said exit duct and diametrically across said container substantially to isolate a first compartment within said container proximate said perforated inlet end containing inert and porous material to filter large particles and retain the contents of the container in position, second separator means located downstream of the first separator means in the gas flow direction substantially to isolate a second compartment containing oxalic acid to remove amines from the gas flow, third separator means located downstream of the second separator means in the gas flow direction substantially to isolate a third compartment containing a metallic salt selected from the group consisting of copper sulphate, mercuric chloride and lead acetate to remove sulfur components from the gas flow and activated charcoal disposed between said third separator means and said hermetically sealed end of the container to envelop the entrance end of the exit duct and remove remaining unpleasant odorous gases.

2. A filter according to claim 1, wherein the inert and porous material is fiberglass.

3. A filter according to claim 1, wherein the inert and porous material is cotton.

4. A filter according to claim 1, wherein the inert and porous material is asbestos.

* * * * *